(12) United States Patent
Gunji et al.

(10) Patent No.: US 7,439,038 B2
(45) Date of Patent: Oct. 21, 2008

(54) METHOD FOR PRODUCING L-AMINO ACID USING METHYLOTROPH

(75) Inventors: Yoshiya Gunji, Kawasaki (JP); Hisashi Yasueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 639 days.

(21) Appl. No.: 10/716,480

(22) Filed: Nov. 20, 2003

(65) Prior Publication Data

US 2004/0146974 A1 Jul. 29, 2004

(30) Foreign Application Priority Data

Nov. 20, 2002 (JP) .............................. 2002-336315

(51) Int. Cl.
*C12P 21/06* (2006.01)
*C12N 9/10* (2006.01)

(52) U.S. Cl. ................... 435/69.1; 435/193; 435/320.1; 435/252; 435/6; 536/23.1

(58) Field of Classification Search ................ 536/23.1, 536/23.4, 23.7, 24.32; 435/320.1, 252.3
See application file for complete search history.

(56) References Cited

U.S. PATENT DOCUMENTS

| | | | | |
|---|---|---|---|---|
| 3,907,637 | A | 9/1975 | Nakayama et al. | ............. 195/29 |
| 3,907,641 | A | 9/1975 | Nakayama et al. | ............. 195/49 |
| 5,217,883 | A | 6/1993 | Anazawa et al. | ......... 435/252.3 |
| 5,972,663 | A | 10/1999 | Winterhalter et al. | .. 435/252.32 |
| 6,303,381 | B1 | 10/2001 | Gunji et al. | |
| 2003/0049804 | A1* | 3/2003 | Pompejus et al. | ........... 435/115 |
| 2003/0049805 | A1 | 3/2003 | Nagase et al. | |
| 2003/0113899 | A1 | 6/2003 | Yamaguchi et al. | |
| 2003/0124687 | A1 | 7/2003 | Gunji et al. | |

FOREIGN PATENT DOCUMENTS

| | | |
|---|---|---|
| AU | 724536 | 7/1997 |
| EP | 1016710 | 7/2000 |
| EP | 1108790 A2 * | 6/2001 |
| EP | 1188822 | 3/2002 |
| EP | 1 266 966 | 12/2002 |
| JP | 45-25273 | 8/1970 |
| JP | 50-25790 | 3/1975 |
| JP | 52-18886 | 2/1977 |
| WO | WO90/12105 | 10/1990 |
| WO | WO 0100843 A3 * | 1/2001 |

OTHER PUBLICATIONS

Brown, T., Hybridization Analysis of DNA Blots, 1993, Current Protocols in Molecular Biology, Chapter 5. p. 2.10.1.*
U.S. Appl. No. 10/716,470, filed Nov. 20, 2003, Gunji et al.
U.S. Appl. No. 10/716,473, filed Nov. 20, 2003, Gunji et al.
Marina Vrljic et al., A new type of transporter with a new type of cellular function: L-lysine export from *Corynebacterium glutamicum*, Molecular Microbiology, 1996, p. 815-826, vol. 22, No. 5.
H. Motoyama et al., Effects of the amplification of the genes coding for the L-threonine biosynthesis enzymes on the L-threonine production from methanol by a gram-negative obligate methylotroph, *Methylobacillus glycogens*, Appl. Microbiol. Biotechnol., 1994, p. 67-72, vol. 42.
L. V. Kletsova et al., Mutants of the obligate methylothroph *Methylobacillus flagellatum* KT defective in genes of the ribulose monophosphate cycle of formaldehyde fixation, Arch. Microbiol., 1988, p. 441-446, vol. 149.
Neil R. Wyborn et al., Molecular characterization of formamidase from *Methylophilus methylotrophus*, Eur. J. Biochem., 1996, p. 314-322, vol. 240.
Owen Jenkins et al., *Methylophilus*: a New Genus of Methanol-Utilizing Bacteria, International Journal of Systematic Bacteriology, Oct. 1987, p. 446-448, vol. 37, No. 4.
Teizi Urakami et al., Emendation of *Methylobacillus*: Yordy and Weaver 1977, a Genus for Methanol-Utilizing Bacteria, International Journal of Systematic Bacteriology, Oct. 1986, p. 502-511, vol. 36, No. 4.
Gunji, Y., et al., "Enhancement of L-lysine production in methylotroph *Methylophilus methylotrophus* by introducing a mutant LysE exporter," J. Biotechnol. 2006;127:1-13.
Motoyama, H., et al., "Amino Acid Production from Methanol by *Methylbacillus glycogens* Mutants: Isolation of L-Glutamic Acid Hyper-producing Mutants from *M. glycogens* Strains, and Derivation of L-Threonine and L-Lysine-producing Mutants from Them," Biosci. Biotech. Biochem. 1993;57(1):82-87.
Motoyama, H., et al., "Overproduction of L-Lysine from Methanol by *Methylobacillus glycogens* Derivatives Carrying a Plasmid with a Mutated dapA Gene," Appl. Environmen. Microbiol. 2001;67(7):3064-3070.
French Patent App. No. 0313574 (Jun. 5, 2007), Search Report.

* cited by examiner

*Primary Examiner*—Hope A Robinson
(74) *Attorney, Agent, or Firm*—Shelly Guest Cermak; Cermak Kenealy & Vaidya LLP

(57) ABSTRACT

A DNA encoding for a mutant of LysE protein, or a homologous protein thereof, of a coryneform bacterium, wherein the mutant, when introduced into a methanol-assimilating bacterium imparts resistance to L-lysine analogue. The DNA encoding for a mutant of LysE protein, or a homologous protein thereof, is introduced into a methanol-assimilating bacterium to improve L-lysine and L-arginine productivity of the methanol-assimilating bacterium.

7 Claims, 1 Drawing Sheet

SEQUENCE LISTING

<160> NUMBER OF SEQ ID NOS: 14

<210> SEQ ID NO 1
<211> LENGTH: 711
<212> TYPE: DNA
<213> ORGANISM: Brevibacterium lactofermentum
<220> FEATURE:
<221> NAME/KEY: CDS
<222> LOCATION: (1)..(711)

<400> SEQUENCE: 1

```
atg gtg atc atg gaa atc ttc att aca ggt ctg ctt ttg ggg gcc agt    48
Met Val Ile Met Glu Ile Phe Ile Thr Gly Leu Leu Leu Gly Ala Ser
  1               5                  10                  15 ctt tta ctg tcc atc gga ccg cag aat gta ctg gtg att aaa caa gga    96
```

```
                                             -continued

Leu Leu Leu Ser Ile Gly Pro Gln Asn Val Leu Val Ile Lys Gln Gly
            20                  25                  30 att aag cgc gaa gga ctc att gcg gtt ctt ctc gtg tgt tta att tct    144
Ile Lys Arg Glu Gly Leu Ile Ala Val Leu Leu Val Cys Leu Ile Ser
         35                  40                  45 gac gtc ttt ttg ttc atc gcc ggc acc ttg ggc gtt gat ctt ttg tcc    192
Asp Val Phe Leu Phe Ile Ala Gly Thr Leu Gly Val Asp Leu Leu Ser
     50                  55                  60 aat gcc gcg ccg atc gtg ctc gat att atg cgc tgg ggt ggc atc gct    240
Asn Ala Ala Pro Ile Val Leu Asp Ile Met Arg Trp Gly Gly Ile Ala
 65                  70                  75                  80 tac ctg tta tgg ttt gcc gtc atg gca gcg aaa gac gcc atg aca aac    288
Tyr Leu Leu Trp Phe Ala Val Met Ala Ala Lys Asp Ala Met Thr Asn
                 85                  90                  95 aag gtg gaa gcg cca cag atc att gaa gaa aca gaa cca acc gtg ccc    336
Lys Val Glu Ala Pro Gln Ile Ile Glu Glu Thr Glu Pro Thr Val Pro
            100                 105                 110 gat gac acg cct ttg ggc ggt tcg gcg gtg gcc act gac acg cgc aac    384
Asp Asp Thr Pro Leu Gly Gly Ser Ala Val Ala Thr Asp Thr Arg Asn
        115                 120                 125 cgg gtg cgg gtg gag gtg agc gtc gat aag cag cgg gtt tgg gta aag    432
Arg Val Arg Val Glu Val Ser Val Asp Lys Gln Arg Val Trp Val Lys
    130                 135                 140 ccc atg ttg atg gca atc gtg ctg acc tgg ttg aac ccg aat gcg tat    480
Pro Met Leu Met Ala Ile Val Leu Thr Trp Leu Asn Pro Asn Ala Tyr
145                 150                 155                 160 ttg gac gcg ttt gtg ttt atc ggc ggt gtc ggc gcg caa tac ggc gac    528
Leu Asp Ala Phe Val Phe Ile Gly Gly Val Gly Ala Gln Tyr Gly Asp
                165                 170                 175 acc gga cgg tgg att ttc gcc gct ggc gcg ttc gcg gca agc ctg atc    576
Thr Gly Arg Trp Ile Phe Ala Ala Gly Ala Phe Ala Ala Ser Leu Ile
            180                 185                 190 tgg ttc ccg ctg gtg ggt ttc ggc gca gca gca ttg tca cgc ccg ctg    624
Trp Phe Pro Leu Val Gly Phe Gly Ala Ala Ala Leu Ser Arg Pro Leu
        195                 200                 205 tcc agc ccc aag gtg tgg cgc tgg atc aac gtc gtc gtg gca gtt gtg    672
Ser Ser Pro Lys Val Trp Arg Trp Ile Asn Val Val Val Ala Val Val
    210                 215                 220 atg acc gca ttg gcc atc aaa ctg atg ttg atg ggt tag                711
Met Thr Ala Leu Ala Ile Lys Leu Met Leu Met Gly
225                 230                 235

<210> SEQ ID NO 2
<211> LENGTH: 236
<212> TYPE: PRT
<213> ORGANISM: Brevibacterium lactofermentum

<400> SEQUENCE: 2

Met Val Ile Met Glu Ile Phe Ile Thr Gly Leu Leu Leu Gly Ala Ser
  1               5                  10                  15

Leu Leu Leu Ser Ile Gly Pro Gln Asn Val Leu Val Ile Lys Gln Gly
             20                  25                  30

Ile Lys Arg Glu Gly Leu Ile Ala Val Leu Leu Val Cys Leu Ile Ser
         35                  40                  45

Asp Val Phe Leu Phe Ile Ala Gly Thr Leu Gly Val Asp Leu Leu Ser
     50                  55                  60

Asn Ala Ala Pro Ile Val Leu Asp Ile Met Arg Trp Gly Gly Ile Ala
 65                  70                  75                  80

Tyr Leu Leu Trp Phe Ala Val Met Ala Ala Lys Asp Ala Met Thr Asn
                 85                  90                  95
```

```
                   85                  90                  95
Lys Val Glu Ala Pro Gln Ile Ile Glu Glu Thr Glu Pro Thr Val Pro
            100                 105                 110

Asp Asp Thr Pro Leu Gly Gly Ser Ala Val Ala Thr Asp Thr Arg Asn
            115                 120                 125

Arg Val Arg Val Glu Val Ser Val Asp Lys Gln Arg Val Trp Val Lys
        130                 135                 140

Pro Met Leu Met Ala Ile Val Leu Thr Trp Leu Asn Pro Asn Ala Tyr
145                 150                 155                 160

Leu Asp Ala Phe Val Phe Ile Gly Gly Val Gly Ala Gln Tyr Gly Asp
                165                 170                 175

Thr Gly Arg Trp Ile Phe Ala Ala Gly Ala Phe Ala Ala Ser Leu Ile
            180                 185                 190

Trp Phe Pro Leu Val Gly Phe Gly Ala Ala Ala Leu Ser Arg Pro Leu
        195                 200                 205

Ser Ser Pro Lys Val Trp Arg Trp Ile Asn Val Val Ala Val Val
            210                 215                 220

Met Thr Ala Leu Ala Ile Lys Leu Met Leu Met Gly
225                 230                 235

<210> SEQ ID NO 3
<211> LENGTH: 1197
<212> TYPE: DNA
<213> ORGANISM: Escherichia coli
<220> FEATURE:
<221> NAME/KEY: CDS
<222> LOCATION: (272)..(1153)

<400> SEQUENCE: 3
ccaggcgact gtcttcaata ttacagccgc aactactgac atgacgggtg atggtgttca      60
caattccacg gcgatcggca cccaacgcag tgatcaccag ataatgtgtt gcgatgacag     120
tgtcaaactg gttattcctt taaggggtga gttgttctta aggaaagcat aaaaaaaaca     180
tgcatacaac aatcagaacg ttctgtctg cttgctttta atgccatacc aaacgtacca     240
ttgagacact tgtttgcaca gaggatggcc c atg ttc acg gga agt att gtc        292
                                   Met Phe Thr Gly Ser Ile Val
                                   1               5 gcg att gtt act ccg atg gat gaa aaa ggt aat gtc tgt cgg gct agc       340
Ala Ile Val Thr Pro Met Asp Glu Lys Gly Asn Val Cys Arg Ala Ser
        10                  15                  20 ttg aaa aaa ctg att gat tat cat gtc gcc agc ggt act tcg gcg atc       388
Leu Lys Lys Leu Ile Asp Tyr His Val Ala Ser Gly Thr Ser Ala Ile
    25                  30                  35 gtt tct gtt ggc acc act ggc gag tcc gct acc tta aat cat gac gaa       436
Val Ser Val Gly Thr Thr Gly Glu Ser Ala Thr Leu Asn His Asp Glu
40                  45                  50                  55 cat gct gat gtg gtg atg atg acg ctg gat ctg gct gat ggg cgc att       484
His Ala Asp Val Val Met Met Thr Leu Asp Leu Ala Asp Gly Arg Ile
                60                  65                  70 ccg gta att gcc ggg acc ggc gct aac gct act gcg gaa gcc att agc       532
Pro Val Ile Ala Gly Thr Gly Ala Asn Ala Thr Ala Glu Ala Ile Ser
            75                  80                  85 ctg acg cag cgc ttc aat gac agt ggt atc gtc ggc tgc ctg acg gta       580
Leu Thr Gln Arg Phe Asn Asp Ser Gly Ile Val Gly Cys Leu Thr Val
        90                  95                 100 acc cct tac tac aat cgt ccg tcg caa gaa ggt ttg tat cag cat ttc       628
Thr Pro Tyr Tyr Asn Arg Pro Ser Gln Glu Gly Leu Tyr Gln His Phe
    105                 110                 115
```

```
aaa gcc atc gct gag cat act gac ctg ccg caa att ctg tat aat gtg    676
Lys Ala Ile Ala Glu His Thr Asp Leu Pro Gln Ile Leu Tyr Asn Val
120                 125                 130                 135 ccg tcc cgt act ggc tgc gat ctg ctc ccg gaa acg gtg ggc cgt ctg    724
Pro Ser Arg Thr Gly Cys Asp Leu Leu Pro Glu Thr Val Gly Arg Leu
                140                 145                 150 gcg aaa gta aaa aat att atc gga atc aaa gag gca aca ggg aac tta    772
Ala Lys Val Lys Asn Ile Ile Gly Ile Lys Glu Ala Thr Gly Asn Leu
        155                 160                 165 acg cgt gta aac cag atc aaa gag ctg gtt tca gat gat ttt gtt ctg    820
Thr Arg Val Asn Gln Ile Lys Glu Leu Val Ser Asp Asp Phe Val Leu
    170                 175                 180 ctg agc ggc gat gat gcg agc gcg ctg gac ttc atg caa ttg ggc ggt    868
Leu Ser Gly Asp Asp Ala Ser Ala Leu Asp Phe Met Gln Leu Gly Gly
185                 190                 195 cat ggg gtt att tcc gtt acg act aac gtc gca gcg cgt gat atg gcc    916
His Gly Val Ile Ser Val Thr Thr Asn Val Ala Ala Arg Asp Met Ala
200                 205                 210                 215 cag atg tgc aaa ctg gca gca gaa gaa cat ttt gcc gag gca cgc gtt    964
Gln Met Cys Lys Leu Ala Ala Glu Glu His Phe Ala Glu Ala Arg Val
                220                 225                 230 att aat cag cgt ctg atg cca tta cac aac aaa cta ttt gtc gaa ccc    1012
Ile Asn Gln Arg Leu Met Pro Leu His Asn Lys Leu Phe Val Glu Pro
        235                 240                 245 aat cca atc ccg gtg aaa tgg gca tgt aag gaa ctg ggt ctt gtg gcg    1060
Asn Pro Ile Pro Val Lys Trp Ala Cys Lys Glu Leu Gly Leu Val Ala
    250                 255                 260 acc gat acg ctg cgc ctg cca atg aca cca atc acc gac agt ggt cgt    1108
Thr Asp Thr Leu Arg Leu Pro Met Thr Pro Ile Thr Asp Ser Gly Arg
265                 270                 275 gag acg gtc aga gcg gcg ctt aag cat gcc ggt ttg ctg taa            1150
Glu Thr Val Arg Ala Ala Leu Lys His Ala Gly Leu Leu
280                 285                 290 agtttaggga gatttgatgg cttactctgt tcaaaagtcg cgcctgg                1197

<210> SEQ ID NO 4
<211> LENGTH: 292
<212> TYPE: PRT
<213> ORGANISM: Escherichia coli

<400> SEQUENCE: 4

Met Phe Thr Gly Ser Ile Val Ala Ile Val Thr Pro Met Asp Glu Lys
 1               5                  10                  15

Gly Asn Val Cys Arg Ala Ser Leu Lys Lys Leu Ile Asp Tyr His Val
                20                  25                  30

Ala Ser Gly Thr Ser Ala Ile Val Ser Val Gly Thr Thr Gly Glu Ser
            35                  40                  45

Ala Thr Leu Asn His Asp Glu His Ala Asp Val Val Met Met Thr Leu
        50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125
```

-continued

```
Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Thr Asn
        195                 200                 205

Val Ala Ala Arg Asp Met Ala Gln Met Cys Lys Leu Ala Ala Glu Glu
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
    290
```

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 5
cgggtggagg tgagcgtcgg taagcagcgg gtttgg          36

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 6 gtcttttgt tcatcaccag caccttgggc gtt             33

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 7
agggaattcc ccgttctgga taatgttttt tgcgccgac      39

<210> SEQ ID NO 8
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 8

```
cggatgcatc tagagttaac ctgcagggtg aaattgttat ccgctcacaa ttccacac        58
```

<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 9

```
catttcctgc aggcaaagga gatgagcgta atggtgatca tggaaatctt cattacaggt        60
ctgc                                                                     64
```

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: primer

SEQUENCE: 10

```
gggcgagcta aagagctcc aaaacccgcg aaaactaacc catcaacatc                    50
```

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 11

```
tgacctgcag gtttgcacag aggatggccc atgtt                                   35
```

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 12

```
cattctagat ccctaaactt tacagcaaac cggcat                                  36
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 13

```
gcacggatca ctgtattcgg ctgcaactt                                          30
```

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 14

```
gccgtgttgc taggatggtt gttcttggat ca                                      32
```

METHOD FOR PRODUCING L-AMINO ACID USING METHYLOTROPH

BACKGROUND OF THE INVENTION

1. Field of the Invention

The present invention relates to a microbial engineering technique useful for production of amino acids and, more specifically to a method for producing L-lysine or L-arginine by fermentation. The present invention also relates to a microorganism useful for the production method.

2. Background Art

L-amino acids such as L-lysine, L-glutamic acid, L-threonine, L-leucine, L-isoleucine, L-valine and L-phenylalanine are industrially produced by fermentation using microorganisms belonging to the genus *Brevibacterium, Corynebacterium, Bacillus, Escherichia, Streptomyces, Pseudomonas, Arthrobacter, Serratia, Penicillium, Candida*, and the like. Bacterial strains isolated from nature or artificial mutants of these bacterial stains are often used in order to improve productivity of these microorganisms. Furthermore, various techniques have been disclosed for increasing L-amino acid production from these stains by enhancing the activity of L-amino acid biosynthetic enzymes using recombinant DNA techniques.

L-amino acid production has been considerably increased by breeding of microorganisms such as those mentioned above and the resulting improvements m the production methods. However, in order to respond to further increases in demand in the future, the development of methods which provide more efficient production of L-amino acids at a lower cost are clearly still necessary, and therefore, still represent a need in the art.

Methanol is a known fermentation raw material which is available in large amounts at a low cost. Methods for producing L-amino acids by fermentation using methanol are known and include methods using microorganisms that belong to the genus *Achromobacter* or *Pseudomonas* (Japanese Patent Publication (Kokoku) No. 45-25273), *Protaminobacter* (Japanese Patent Laid-Open Publication (Kokai) No. 49-125590), *Protaminobacter* or *Methanoinonas* (Japanese Patent Laid-open Publication (Kokai) No. 50-25790), *Microcyclus* (Japanese Patent Laid-open Publication (Kokai) No. 52-18886), *Methylobacillus* (Japanese Patent Laid-open Publication (Kokai) No. 4-91793), *Bacillus* (Japanese translation of PCT international application Patent (Kohyo) No. 3-505284 (WO90/12105)) and so forth. The inventors of the present invention have developed methods for producing L-amino acids by breeding bacteria belonging to the genus *Methylophilus* and *Methylobacillus* using artificial mutagenesis and recombinant DNA techniques (International Publication WO00/61723; Japanese Patent Laid-open Publication (Kokai) No. 2001-120269).

In recent years proteins have been identified that have a function of specifically secreting an L-amino acid to the outside of a cell or microorganism, as well as the genes which encode these proteins. In particular, Vrljic et al. have identified a gene involved in the secretion of L-lysine from a *Corynebacterium* bacterium to the outside of a cell (Molecular Microbiology 22:815-826 (1996)). This gene was designated as lysE, and it was reported that L-lysine producing ability of *Corynebacterium* bacteria could be improved by enhancing the expression of this gene in the bacteria (International Publication WO97/23597). It is also known that production of several kinds of L-amino acids can be improved by increasing expression amounts of amino acid secreting proteins in *Escherichia coli* (Japanese Patent Laid-open Publication No. 2000-189180). For example, it has been reported that production of cystine, cysteine, and so forth can be improved by enhancing the expression of ORF306 gene in *Escherichia coli* (European Patent Laid-open Publication No. 885962).

However, there have been no reports to date on improving the L-amino acid production by enhancing their secretion during fermentation of methanol-assimilating bacteria. Furthermore, no amino acid secretion gene that can exhibit secretion activity in methanol-assimilating bacteria has been reported.

SUMMARY OF THE INVENTION

An object of the present invention is to provide a method for efficiently producing L-lysine or L-arginine using methanol, which is abundantly and inexpensively available.

It is a further object of the present invention to provide a DNA encoding for a mutant of LysE protein, or a homologous protein thereof, of a coryneform bacterium, wherein the mutant, or homologous protein thereof, when introduced into a methanol-assimilating bacterium imparts resistance to a L-lysine analogue.

It is a further object of the present invention to provide a DNA as stated above, wherein the mutant is a protein defined as the following (A) or (B): (A) a protein which has the amino acid sequence of SEQ ID NO: 2, whereby at least the glycine residue at position 56 is replaced by another amino acid, or (B) a protein which has the amino acid sequence of SEQ ID NO: 2 whereby at least the glycine residue at position 56 is replaced with another amino acid residue, and one or several amino acid residues at positions other than the 56th residue are substituted, deleted, inserted or added, and when said mutant is introduced into a methanol-assimilating bacterium, imparts resistance to a L-lysine analogue.

It is even a further object of the present invention to provide the DNA as stated above, wherein said DNA is selected from the group consisting of A) a DNA which has the nucleotide sequence of SEQ ID NO: 1, whereby a mutation results in replacement of at least the 56th glycine residue of the encoded protein with another amino acid residue, or B) a DNA which is hybridizable with the nucleotide sequence of SEQ ID NO: 1 under the stringent conditions, or a probe prepared from said nucleotide sequence, which when introduced into a methanol-assimilating bacterium, imparts resistance to L-lysine analogue.

It is even a further object of the present invention to provide the DNA as stated above, wherein the other amino acid residue is a serine residue.

It is even a further object of the present invention to provide the DNA as stated above, wherein the L-lysine analogue is S-(2-aminoethyl)cysteine.

It is even a further object of the present invention to provide the DNA as stated above, wherein the methanol-assimilating bacterium is a bacterium belonging to the genus *Methylophilus* or *Methylobacillus*.

It is even a further object of the present invention to provide a bacterium belonging to the genus *Methylophilus* or *Methylobacillus*, into which the DNA as described above in an expressible form is introduced and which has L-lysine or L-arginine producing ability.

It is even a further object of the present invention to provide a method for producing L-lysine or L-arginine comprising the steps of A) culturing the bacterium as described above in a medium to produce and accumulate L-lysine or L-arginine in the culture, and B) collecting L-lysine or L-arginine from the culture.

It is even a further object of the present invention to provide the method as stated above, wherein the medium contains methanol as a main carbon source.

According to the present invention, the L-amino acid productivity of methanol-assimilating bacteria, especially productivity of L-lysine and L-arginine, can be improved.

DETAILED DESCRIPTION OF THE INVENTION

Figure 1:
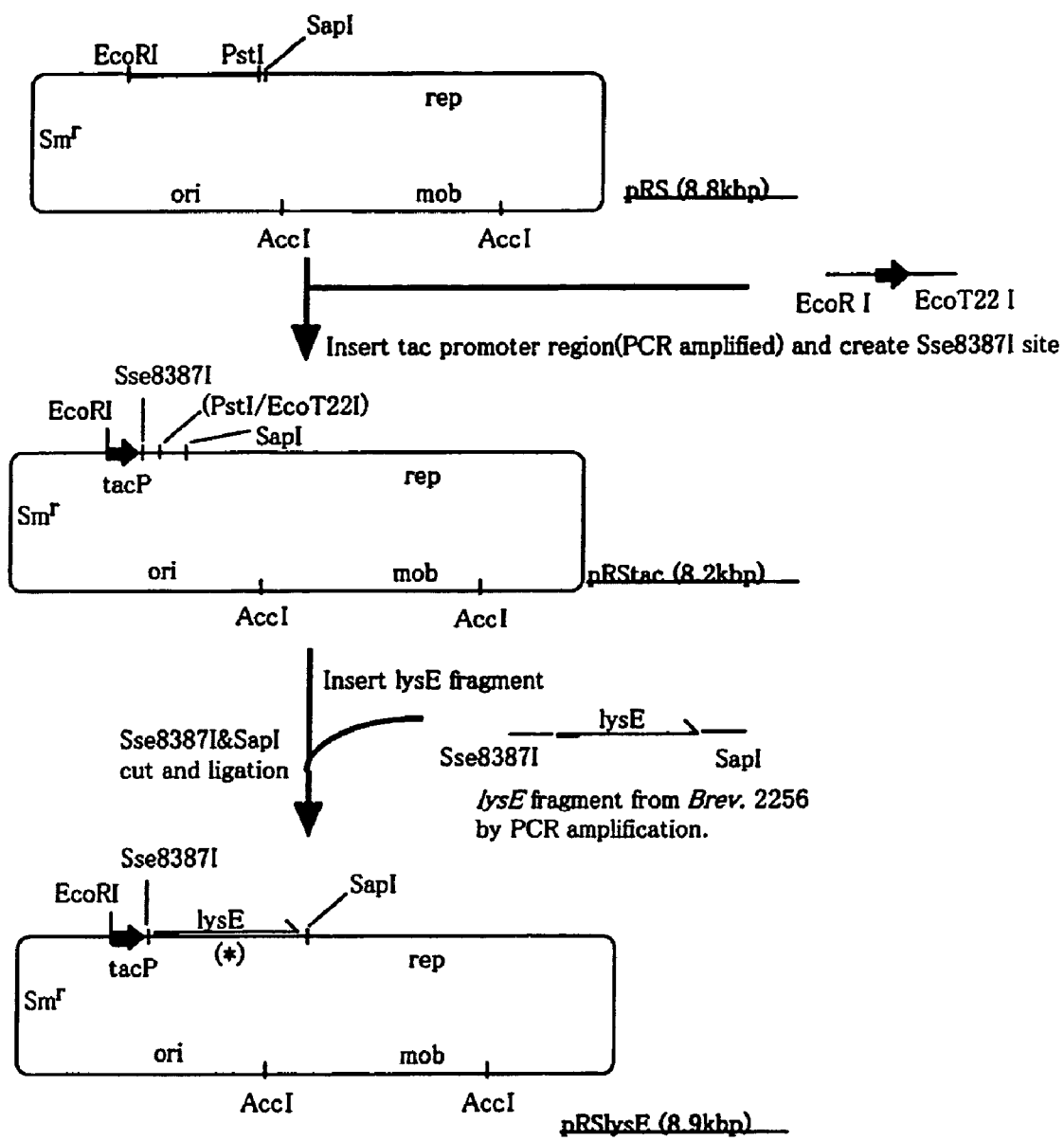
FIG. 1 shows a map of a plasmid pRStac having the tac promoter and a plasmid pRSlysE, which was constructed by inserting the lysE gene into pRStac.

The inventors of the present invention assiduously studied to achieve the above-referenced objects of the present invention Initially, they found that when an L-amino acid, in particular, L-lysine or L-arginine, is produced using methanol-assimilating bacteria, in particular, bacteria belonging to the genus *Methylophilus* and *Methylobacillus*, the extracellular secretion process of these L-amino acids was unsuccessful. Then, the inventors were able to successfully obtain genes which exhibited an activity for secreting amino acids, especially in these microorganisms, and thus found that amino acids could be efficiently produced by utilizing the thus-obtained genes.

The inventors of the present invention introduced the already known lysE gene from *Corynebacterium* bacterium into a methanol-assimilating bacterium, and examined its effect on the amino acid production. It was found that introduction of the lysE gene into a methanol-assimilating bacterium resulted in mutation or deletion, and thus lysE could not function. Proteins responsible for secretion typically need to be incorporated into the cell membrane in order to function, therefore, the protein and membrane conditions such as lipid composition must be suitable for each other. It was concluded that it would be difficult to express a heterologous membrane protein, such as LysE, so that the protein can function, and this conclusion was supported by the aforementioned result.

Therefore, the inventors of the present invention found a mutant gene that could function in a methanol-assimilating bacterium while researching the aforementioned L-amino acid secretion gene. Furthermore, they found a marked effect upon use of this mutant gene in amino acid production using a methanol-assimilating bacteria. They further advanced the research and successfully obtained a plurality of mutant genes that can function in methanol-assimilating bacteria.

Hereinafter, the present invention will be explained in detail.

DNA of the Present Invention

The DNA of the present invention encodes a mutant of the LysE protein, or a homologous protein of the LysE protein, derived from a coryneform bacterium, which can exhibit a function of the LysE protein when it is introduced into a methanol-assimilating bacterium.

The "function of the LysE protein" as used herein means at least one of the functions defined as follows (1 and/or 2):

(1) Function of Imparting Resistance to L-Lysine Analogue When Expressed in a Methanol-Assimilating Bacterium upon Introduction of the Aforementioned DNA Encoding the Mutant.

The expression "imparting resistance to L-lysine analogue" to the bacterium as used herein means that upon introduction of the aforementioned DNA encoding the LysE mutant into the aforementioned methanol-assimilating bacterium, the bacterium is able to grow in the presence of a higher concentration of L-lysine analogues compared with bacteria which do not contain the DNA, for example, wild-type strains of the methanol-assimilating bacteria. For example, after culture on an agar medium containing an L-lysine analogue at a certain concentration for a certain period, if a transformant strain of the methanol-assimilating bacterium introduced with the aforementioned DNA forms colonies, but a non-transformant strain does not form colonies, the aforementioned transformant strain is imparted with resistance to the L-lysine analogue. Examples of the L-lysine analogue include S-(2-aminoethyl)cysteine.

(2) Function of Enhancing Extracellular Secretion of One or Both of L-Lysine or L-Arginine, When the Aforementioned Mutant is Introduced into a Methanol-Assimilating Bacterium The expression of "enhancing extracellular secretion of one or both of L-lysine or L-arginine" as used herein means that, when a methanol-assimilating bacterium containing the DNA of the present invention is cultured, the amount of one or both of L-lysine or L-arginine secreted into a medium is increased compared with the methanol-assimilating bacterium which does not contain the DNA of the present invention. The enhancement of extracellular secretion of the L-amino acid is observed by an increased concentration of the L-amino acid accumulated in the medium during culture of a methanol-assimilating bacterium containing the DNA of the present invention compared with the methanol-assimilating bacterium not containing the DNA of the present invention, as a result of the introduction of the DNA. Furthermore, the enhancement of extracellular secretion of the L-amino acid can also be observed when a decreased intracellular L-amino acid concentration is detected upon introduction of the DNA of the present invention into a methanol-assimilating bacterium.

In the present invention, the methanol-assimilating bacterium, that is, methylotroph, means a bacterium which can grow by utilizing methanol as a major carbon source. Specific examples include *Methylophilus* bacteria such as *Methylophilus methylotrophus* and *Methylobacillus* bacteria such as *Methylobacillus glycogenes* and *Methylobacillus flagellatum*.

Examples of *Methylophilus methylotrophus* include, but are not limited to the AS1 strain (NCIMB10515) and so forth. The *Methylophilus methylotrophus* AS1 strain (NCIMB10515) is available from the National Collections of Industrial and Marine Bacteria (Address: NCIMB Lts., Torry Research Station, 135, Abbey Road, Aberdeen AB9 8DG, United Kingdom).

Examples of *Methylobacillus glycogenes* include, but are not limited to the T-11 strain (NCIMB 11375), ATCC 21276 strain, ATCC 21371 strain, ATR80 strain (described in Appl. Microbiol. Biotechnol., 42, pp.67-72 (1994)),A513 strain (described in Appl. Microbiol. Biotechnol., 42, pp.67-72 (1994)) and so forth. The *Methylobacillus glycogenes* NCIMB 11375 strain is available from the National Collections of Industrial and Marine Bacteria (Address: NCIMB Lts., Torry Research Station, 135, Abbey Road, Aberdeen AB9 8DG, United Kingdom). Examples of *Methylobacillus flagellatum* include, but are not limited to the KT strain (described in Arch. Microbiol., 149, pp.441-446 (1988)) and so forth.

One embodiment of the DNA of the present invention is a DNA encoding for a protein which has the amino acid sequence of SEQ ID NO: 2, whereby at least the glycine residue at position 56 is replaced with another amino acid residue.

Furthermore, a more specific embodiment of the DNA of the present invention is a DNA encoding for a protein which has the amino acid sequence of SEQ ID NO: 2 and includes a mutation for any of the following:

(i) replacement of the glycine residue at position 56 in SEQ ID NO: 2 with another amino acid residue;

(ii) replacement of the glycine residue at position 56 in SEQ ID NO: 2 with another amino acid residue, and replacement of the alanine residue at position 55 in SEQ ID NO: 2 with another amino acid residue;

(iii) replacement of the glycine residue at position 56 in SEQ ID NO: 2 with another amino acid residue, and replacement of the aspartic acid residue at position 137 in SEQ ID NO: 2 with another amino acid residue.

Specific examples of the replacement at the 56th position include, but are not limited to replacement of the glycine residue with a serine residue. Specific examples of the replacement at the 55th position include, but are not limited to replacement of the alanine residue with a threonine residue. Specific examples of replacement at the 137th position include, but are not limited to replacement of the aspartic acid residue with a glycine residue.

More specific embodiments of the DNA of the present invention encoding proteins having the aforementioned replacements are DNAs designated as lysE562, lysE564 and lysE565 described herein in the examples. These are mutants of genes isolated from *Brevibacterium lactofermentum* as homologues of the lysE gene reported for *Corynebacterium* bacteria. Therefore, the DNA of the present invention is also referred to as "mutant lysE," and the protein encoded by the DNA of the present invention as "mutant LysE," for convenience.

As a DNA encoding for the LysE protein of coryneform bacteria, the nucleotide sequence of wild-type lysE of *Brevibacterium lactofermentum* is shown in SEQ ID NO: 1, and the amino acid sequence of the encoded protein is shown in SEQ ID NO: 2.

It was found that the glycine at the 56th position from the amino terminus is changed to serine in the amino acid sequence of the protein encoded by lysE564, as compared to the amino acid sequence of SEQ ID NO: 2 encoded by wild-type lysE. It was found that the glycine at the 56th position from the amino terminus is changed to serine and aspartic acid at the 137th position is changed to glycine in the amino acid sequence of the protein encoded by lysE562, as compared to the amino acid sequence of SEQ ID NO: 2 encoded by wild-type lysE It was also found that the glycine at the 56th position from the amino terminus is changed to serine, and the alanine at the 55th position is changed to threonine in the amino acid sequence of the protein encoded by lysE565 as compared with the amino acid sequence encoded by wild-type lysE. The common mutation point was found to be the replacement of glycine with serine at the 56th position. It was determined that the change at this position was important, in particular, for production of a secretion carrier which has an activity of secretion of L-lysine in a methylotroph.

The DNA of the present invention may encode an amino acid sequence including substitution, deletion, insertion or addition of one or several amino acid residues at positions other than the 55$^{th}$, 56$^{th}$ and 137th positions so long as the encoded mutant LysE has any of the aforementioned mutations and exhibits the function of the LysE protein in a methanol-assimilating bacterium. The term "several" as used herein varies depending on the positions of amino acid residues in the three-dimensional structure of the protein and the types of the amino acids. However, it preferably means between 2 to 10 amino acid residues, more preferably between 2 to 5, and most preferably between 2 to 3.

A DNA encoding for a protein substantially identical to the aforementioned mutant LysE can be obtained by modifying the nucleotide sequence of the mutant lysE For example, site-directed mutagenesis can be employed so that substitution, deletion, insertion or addition of an amino acid residue or residues occurs at a specific site. Furthermore, a DNA modified as described above can also be obtained by conventionally-known mutation treatments. Examples of such mutation treatments include a method of treating the DNA before the mutation treatment in vitro with hydroxylamine or the like, a method of treating a microorganism, for example, an *Escherichia* bacterium, containing DNA before the mutation treatment with ultraviolet ray irradiation or a mutagenesis agent used in a usual mutation treatment such as N-methyl-N'-nitro-N-nitrosoguanidine (NTG) or nitrous acid, and so forth. These methods are described in Sambrook, J., Fritsch, E. F., and Maniatis, T., "Molecular Cloning A Laboratory Manual, Second Edition", Cold Spring Harbor Laboratory Press (1989) and so forth.

A DNA encoding for a protein substantially identical to the mutant LysE can be obtained by expressing a DNA including any of the aforementioned mutations in a methanol-assimilating bacterium and examining the activity of the expression product In the present invention, the positions of the amino acid residues are not necessarily absolute positions in each LysE protein, but positions relative to the positions in the amino acid sequence of SEQ ID NO: 2. For example, when one amino acid residue is deleted on the N-terminus side of the 56th position in the amino acid sequence of SEQ ID NO: 2, the aforementioned 56th amino acid residue becomes the 55th amino acid residue from the N-terminus. In this case, since the 55th amino acid residue from the N-terminus is an amino acid residue corresponding to the 56th amino acid residue in SEQ ID NO: 2, it is the "56th" amino acid residue.

The DNA encoding LysE protein of coryneform bacterium or its homologue protein, i.e., the lysE gene or its homologous gene, may be obtained from any microorganism, so long as the microorganism has variants of genes that can express the L-lysine secretion activity in a methanol-assimilating bacterium. Specifically, examples of such microorganisms include, but are not limited to, coryneform bacteria such as *Corynebacterium glutamicum* and *Brevibacterium lactofermentum*, *Escherichia* bacteria such as *Escherichia coli*, *Pseudomonas* bacteria such as *Pseudomonas aeruginosa*, *Mycobacterium* bacteria such as *Mycobacterium tuberculosis* and so forth.

Examples of the homologous gene to lysE include a DNA encoding for a protein, which is hybridizable with a probe having the nucleotide sequence of SEQ ID NO: 1 or a part thereof under stringent conditions, and codes for a protein which exhibits the function of the LysE protein in a methanol-assimilating bacterium as a result of the aforementioned amino acid substitution. The aforementioned "stringent conditions" include a condition under which a so-called specific hybrid is formed, and a non-specific hybrid is not formed. It is difficult to clearly express this condition by using any numerical value. However, for example, the stringent conditions include a condition whereby DNAs having high homology, for example, DNAs having homology of 80% or more, preferably 90% or more, more preferably 95% or more, are hybridized with each other, whereas DNAs having homology lower than the above do not hybridize with each other. Alternatively, the stringent conditions are exemplified by conditions whereby DNAs hybridize with each other at a salt concentration upon ordinary conditions of washing in Southern hybridization, i.e., 1×SSC, 0.1% SDS, preferably 0.1×SSC, 0.1% SDS, at 60° C.

A partial sequence of the nucleotide sequence of SEQ ID NO: 1 can also be used as the probe. Probes can be generated by PCR using oligonucleotides based on the nucleotide sequence of SEQ ID NO: 1 as primers, and a DNA fragment containing the nucleotide sequence of SEQ ID NO: 1 as a template. When a DNA fragment of about 300 bp is used as the probe, the washing conditions of hybridization can be, for example, 2×SSC, 0.1% SDS at 50° C.

In order to enhance the mutant lysE gene expression in a methanol-assimilating bacterium such as *Methylophilus* bacteria or *Methylobacillus* bacteria, the gene fragment containing the mutant lysE gene can be ligated to a vector that functions in a methanol-assimilating bacterium, preferably a multi-copy type vector, to prepare recombinant DNA and used to transform a host such as a methanol-assimilating bacterium. Alternatively, the mutant lysE gene may be incorporated into a transposon and introduced into the chromosome. Furthermore, a promoter that induces potent transcription in a methanol-assimilating bacterium can be ligated to the upstream of the mutant lysE gene.

The reference WO97/23597 discloses lysE, and only shows the lysE gene of coryneform bacterium introduced into a coryneform bacterium. Furthermore, it only mentions L-lysine as the secreted amino acid, and discloses a novel protein secretion system, including LysE having a structure containing six transmembrane helixes. However, the inventors of the present invention confirmed that LysE derived from coryneform bacteria did not function at all in methanol-assimilating bacteria Furthermore, the obtained factor is a novel L-lysine secretion carrier that includes a substitution mutation of an amino acid at a specific site, and such a factor cannot be inferred at all from the previous patent specifications concerning lysE.

Methanol-Assimilating Bacterium of the Present Invention

The methanol-assimilating bacterium of the present invention is a methanol-assimilating bacterium into which the aforementioned DNA of the present invention in an expressible form is introduced and which has L-lysine- or L-arginine-producing ability. The methanol-assimilating bacterium of the present invention can be obtained by introducing the DNA of the present invention into a methanol-assimilating bacterium having L-lysine- or L-arginine-producing ability. The methanol-assimilating bacterium of the present invention can also be obtained by imparting L-lysine- or L-arginine-producing ability to a methanol-assimilating bacterium introduced with the DNA of the present invention. Furthermore, the methanol-assimilating bacterium of the present invention may be a bacterium imparted with the L-lysine- or L-arginine-producing ability by introducing the DNA of the present invention in an expressible form.

Examples of the methanol-assimilating bacterium include, but are not limited to the aforementioned *Methylophilus* bacteria or *Methylobacillus* bacteria A methanol-assimilating bacterium having L-lysine- or L-arginine-producing ability can be obtained by imparting an L-lysine- or L-arginine-producing ability to a wild-type strain of a methanol-assimilating bacterium. Methods conventionally used for breeding of coryneform bacteria, *Escherichia* bacteria and so forth, can be used to impart the L-lysine- or L-arginine-producing ability. For example, such methods include, but are not limited to acquisition of auxotrophic mutant strains, analogue resistant stains or metabolic regulation mutant strains, creation of recombinant strains in which an L-lysine or L-arginine biosynthesis system enzyme is enhanced (see "Amino Acid Fermentation", the Japan Scientific Societies Press [Gakkai Shuppan Center], 1st Edition, published on May 30, 1986, pp.77 to 100) and so forth. Properties of auxotrophy, analogue resistance, metabolic regulation mutation and so forth may be individually imparted or two or more may be imparted in combination when breeding L-lysine- or L-arginine-producing bacteria. The biosynthesis system enzyme may be individually enhanced or two or more of them may be enhanced in combination. Furthermore, the impartation of properties including auxotrophy, analogue resistance, metabolic regulation mutation and so forth may be combined with the enhancement of biosynthesis system enzyme.

For example, L-lysine-producing bacteria can be bred to be auxotrophic for L-homoserine or L-threonine and L-methionine (Japanese Patent Publication Nos. 48-28078 and 56-6499), or be auxotrophic for inositol or acetic acid (Japanese Patent Laid-open Nos. 55-9784 and 56-8692), or be resistant to oxalysine, lysine hydroxamate, S(2-aminoethyl)-cysteine, γ-methyllysine, α-chlorocaprolactam, DL-α-amino-ε-caprolactam, α-amino-lauryllactam, aspartic acid analogue, a sulfa drug, quinoid or N-lauroylleucine.

L-arginine-producing bacteria can be bred to be resistant to a certain agent, for example, a sulfa drug, 2-thiazolealanine, α-amino-β-hydroxyvaleric acid or the like; to be auxotrophic for L-histidine, L-proline, L-threonine, L-isoleucine, L-methionine or L-tryptophan in addition to resistance to 2-thiazolealanine (Japanese Patent Laid-open No. 54-44096); to be resistant to ketomalonic acid, fluoromalonic acid monofluoroacetic acid (Japanese Patent Laid-open No. 57-18989); to be resistant to argininol (Japanese Patent Laid-open No. 62-24075); to be resistant to X-guanidine (X represents a derivative of fatty acid or aliphatic chain, Japanese Patent Laid-open No. 2-186995); to be resistant to 5-azauracil, 6-azauracil, 2-thiouracil, 5-fluorouracil, 5-bromouracil, 5-azacytosine, 6-azacytosine and so forth, to be resistant to arginine hydroxamate and 2-thiouracil; to be resistant to arginine hydroxamate and 6-azauracil (see Japanese Patent Laid-open No. 57-150381); to be resistant to a histidine analogue or tryptophan analogue (see Japanese Patent Laid-open No. 52-114092); to be auxotrophic for at least one of methionine, histidine, threonine, proline, isoleucine, lysine, adenine, guanine and uracil (or uracil precursor) (see Japanese Patent Laid-open No. 52-99289); to be resistant to arginine hydroxamate (see Japanese Patent Publication No. 51-6754); to be auxotrophic for succinic acid or resistant to a nucleic acid base analogue (see Japanese Patent Laid-open No. 58-9692); to be unable to metabolize arginine and to be resistant to an arginine antagonist and canavanine and to be auxotorophic for lysine (see Japanese Patent Laid-open No. 52-8729); to be resistant to arginine, arginine hydroxamate, homoarginine, D-arginine and canavanine, or resistant to arginine hydroxamate and 6-azauracil (see Japanese Patent Laid-open No. 53-143288); to be resistant to canavanine (see Japanese Patent Laid-open No. 53-3586) and so forth.

Hereinafter, methods for imparting or enhancing L-amino acid-producing ability by enhancing an L-amino acid biosynthetic enzyme gene are exemplified.

L-lysine-producing ability can be imparted by, for example, enhancing activities of dihydrodipicolinate synthase and aspartokinase. The activities of dihydrodipicolinate synthase and aspartokinase in a methanol-assimilating bacterium can be enhanced by transforming the methanol-assimilating bacterium host with a recombinant DNA, which has been prepared by ligating a gene fragment encoding dihydrodipicolinate synthase and a gene fragment encoding aspartokinase with a vector that functions in the methanol-assimilating bacterium, preferably a multiple copy type vector. The activities of dihydrodipicolinate synthase and aspartokinase are enhanced as a result of the increase in copy numbers of the genes encoding the enzymes in the transformant strain. Hereinafter, dihydrodipicolinate synthase, aspartokinase and aspartokinase III are also referred to as DDPS, AK and AKIII, respectively.

Any microorganism may provide the genes which encode DDPS and AK, so long as the chosen microorganism harbors genes which can express DDPS activity and AK activity in a methanol-assimilating bacterium. Such microorganisms may be wild-type stains or mutant strains derived therefrom. Specifically, examples of such microorganisms include, but are not limited to *E. coli* (*Escherichia coli*) K-12 stain, *Methylophilus methylotrophus* AS1 strain (NCIMB10515) and *Methylobacillus glycogenes* T-11 strain (NCIMB 11375) and so forth. These genes can be obtained by PCR using primers synthesized based on the known nucleotide sequences of DDPS (dapA, Richaud, F. et al., J. Bacteriol., 297 (1986)) and AKIII (lysC, Cassan, M., Parsot, C., Cohen, G N. and Patte, J. C., J. Biol. Chem., 261, 1052 (1986)) and using chromosomal DNA from a microorganism such as *E. coli* K-12 as a template. Specific examples include, but are not limited to dapA and lysC derived from *E. coli*, as explained herein.

Preferably, the DDPS and AK used in the present invention will not be subject to feedback inhibition by L-lysine. It is known that wild-type DDPS derived from *E. coli* is subject to feedback inhibition by L-lysine (see U.S. Pat. Nos. 5,661,012 and 6,040,160) and that wild-type AKIII derived from *E. coli* is subject to suppression and feedback inhibition by L-lysine. Therefore, dapA and lysC preferably encode for DDPS and AKIII, respectively, each of which contain a mutation that eliminates the feedback inhibition by L-lysine upon introduction into a methanol-assimilating bacterium. Hereinafter, DDPS which contains a mutation that eliminates the feedback inhibition by L-lysine may also be referred to as "mutant DDPS," and DNA encoding the mutant DDPS may also be referred to as "mutant dapA," or "dapA*." AKIII derived from *E. coli* which contains a mutation that eliminates the feedback inhibition by L-lysine may also be referred to as "mutant AKIII," and DNA encoding the mutant AKIII may also be referred to as "mutant lysC."

However, it is not always necessary that DDPS and AK be mutated in the present invention. It is known that, for example, DDPS derived from *Corynebacterium* bacteria does not suffer feedback inhibition by L-lysine (see Korean Patent Publication No. 92-8382, U.S. Pat. Nos. 5,661,012 and 6,040,160).

A nucleotide sequence of wild-type dapA derived from *E. coli* is exemplified in SEQ ID NO: 3, and the amino acid sequence of wild-type DDPS encoded by this nucleotide sequence is exemplified in SEQ ID NO: 4.

The DNA encoding mutant DDPS that does not suffer feedback inhibition by L-lysine may be a DNA encoding DDPS having the amino acid sequence of SEQ ID NO: 4, including replacing the histidine residue at position 118 of SEQ ID NO: 4 with a tyrosine residue. Furthermore, the DNA encoding mutant AKIII that does not suffer feedback inhibition by L-lysine may be a DNA encoding AKIII having the amino acid sequence including replacing the threonine at position 352 with an isoleucine residue (for the AKIII sequence, see U.S. Pat. Nos. 5,661,012 and 6,040,160).

The plasmid used for gene cloning may be any plasmid so long as it can replicate in microorganisms such as *Escherichia* bacteria. Specifically, examples of such bacteria include pBR322, pTWV228, pMW119, pUC19 and so forth.

Vectors that functions in *Methylophilus* bacteria include, for example, a plasmid that can autonomously replicate in *Methylophilus* bacteria. Specifically, examples include RSF1010, which is a broad host spectrum vector, and derivatives thereof, pAYC32 (Chistorerdov, A. Y., Tsygankov, Y. D. Plasmid, 16, 161-167 (1986)), pMFY42 (Gene, 44, 53 (1990)), pRP301, pTB70 (Nature, 287, 396, (1980)) and so forth.

Furthermore, examples of vectors that function in *Methylobacillus* bacteria include, for example, a plasmid that can autonomously replicate in *Methylobacillus* bacteria Specific examples include RSF1010, which is a broad host spectrum vector, and derivatives thereof such as pMFY42 (Gene, 44, 53 (1990)).

To prepare a recombinant DNA via ligation of dapA and lysC to a vector that functions in a methanol-assimilating bacterium, the vector is digested with a restriction enzyme suitable for the ends of a DNA fragment containing dapA and lysC. The ligation is usually performed by using a ligase such as T4 DNA ligase. The genes dapA and lysC may be incorporated into separate vectors or the same vector.

A wide host range plasmid RSFD80 is known (WO95/16042), and may be used in the present invention as the plasmid having a mutant dapA encoding for a mutant DDPS and a mutant lysC encoding for a mutant AKIII. An *E. coli* JM 109 strain transformed with this plasmid was designated as AJ12396, and deposited at National Institute of Bioscience of Advanced Industrial Science and Technology on Oct. 28, 1993, receiving an accession number of FERM P-13936. Then, it was transferred to an international deposit under the provisions of the Budapest Treaty on Nov. 1, 1994 and received an accession number of FERM BP-4859. RSFD80 can be obtained from the AJ12396 strain by a known method.

RSFD80 contains a mutant dapA. wherein the nucleotide sequence of wild-type dapA shown in SEQ ID NO: 3 is changed at position 623 from C to T. The histidine residue at position 118 of the wild-type DDPS of Seq ID No. 4, which is encoded by the wild-type dapA of Seq ID No. 3, is changed to a tyrosine residue as a result of the above nucleotide change. Furthermore, RSFD80 contains a mutant lysC, wherein the nucleotide sequence of wild-type lysC is changed at position 1638 from C to T. This mutation results in the mutant AKIII, however the threonine at position 352 is changed to a isoleucine.

Any method can be used to introduce the recombinant DNA prepared as described above into a *Methylophilus* bacterium or *Methylobacillus* bacterium, so long as it provides sufficient transformation efficiency. For example, electroporation can be used (Canadian Journal of Microbiology, 43, 197 (1997)).

Enhancing the expression of a desired gene can be accomplished by introducing multiple copies of the gene on chromosomal DNA of a *Methylophilus* bacterium. Multiple copies of dapA and lysC may be introduced into the chromosomal DNA of a *Methylophilus* bacterium by homologous recombination. This can be performed by targeting a sequence present on chromosomal DNA in multiple copy number. A repetitive DNA or an inverted repeat present at the end of a transposable element can be used as the sequence present on chromosomal DNA in multiple copy number. Alternatively, as disclosed in Japanese Patent Laid-open No. 2-109985, multiple copies of the desired gene can be introduced into chromosomal DNA by incorporating them into a transposon and transferring it In both of the methods, activity of the desired genes will be amplified as a result of increased copy numbers of desired genes in transformant strains.

Besides the above gene amplification methods, expression of the desired gene can be enhanced by replacing an expression control sequence, such as promoters of dapA and lysC, with stronger ones (see Japanese Patent Laid-open No. 1-215280). Examples of strong promoters, include lac promoter, trp promoter, trc promoter, tac promoter, PR promoter and PL promoter of lambda phage, tet promoter, amyE promoter, spac promoter and so forth. Use of these promoters enhances expression of the desired gene, and thus the activity of the desired gene product is amplified. Such gene expression enhancement methods can be combined with the gene amplification (increasing the copy number of the desired gene) methods described above.

Preparation of a recombinant DNA can be accomplished by ligating a gene fragment and a vector once the vector is digested with a restriction enzyme corresponding to the terminus of the gene fragment. Ligation is usually performed by ligase such as T4 DNA ligase. The usual methods well known to those with skill in the art can be used as methods for digestion, and include ligation of DNA, preparation of chromosomal DNA, PCR, preparation of plasmid DNA, transformation, design of oligonucleotides used as primers and so forth. Such methods are described in Sambrook, J., Fritsch, E. F., and Maniatis, T., "Molecular Cloning A Laboratory Manual, Second Edition", Cold Spring Harbor Laboratory Press (1989) and so forth.

In addition to the enhancement of DDPS and AK gene expression or activity, other enzymes involved in the L-lysine biosynthesis may also be enhanced. Such enzymes include diaminopimelate pathway enzymes such as dihydrodipicolinate reductase, diaminopimelate decarboxylase, diaminopimelate dehydrogenase (see WO96/40934 for all of the foregoing enzymes), phosphoenolpyruvate carboxylase (Japanese Patent Laid-open No. 60-87788), aspartate aminotransferase (Japanese Patent Publication No. 6-102028), diaminopimelate epimerase and aspartic acid semialdehyde dehydrogenase, aminoadipate pathway enzymes such as homoaconitate hydratase and so forth.

Aspartokinase, aspartic acid semialdehyde dehydrogenase, dihydrodipicolinate synthase, dihydrodipicoilnate reductase and diaminopimelate decarboxylase derived from *Methylophilus methylotrophus* are described in WO 00/61723.

Furthermore, the microorganism of the present invention may have decreased activity of an enzyme that catalyzes a reaction for generating a compound other than L-lysine by branching off from the biosynthetic pathway for L-lysine, or may be deficient in such an enzyme. Illustrative examples of the enzyme that catalyzes a reaction for generating a compound other than L-lysine by branching off from the biosynthetic pathway for L-lysine include homoserine dehydrogenase (see WO95/23864).

The aforementioned techniques for enhancing activities of enzymes involved in the L-lysine biosynthesis can be similarly used for L-arginine.

L-arginine-producing ability can be improved by enhancing acetylornithine deacetylase activity, N-acetylglutamic acid-g-semialdehyde dehydrogenase activity, N-acetyl glutamokinase activity and argininosuccinase activity (see Japanese Patent Publication No. 5-23750).

L-arginine-producing ability can also be improved by enhancing activity of glutamate dehydrogenase (EP 1 057 893 A1), argininosuccinate synthase (EP0 999 267 A1), carbamoyl phosphate synthetase (EP1 026 247 A1) or N-acetylglutamate synthase (see Japanese Patent Laid-open No. 57-5693) or by disrupting the gene encoding an arginine repressor (argR).

Production of L-lysine or L-arginine

L-lysine or L-arginine can be produced by culturing a methanol-assimilating bacterium, such as *Methylophilus* bacteria or *Methylobacillus* bacteria, having L-lysine- or L-arginine-producing ability. L-lysine or L-arginine can be obtained as described above from the medium upon production and accumulation. L-lysine or L-arginine can then be collected from the culture.

The microorganism used in the present invention can be cultured by a method typically used in culture of methanol-assimilating microorganisms. Either a natural medium or synthetic medium may be used as the medium in the present invention, so long as it contains a carbon source, a nitrogen source, inorganic ions and other organic trace amount components as required.

If methanol is used as a main carbon source, L-lysine or L-arginine can be produced at a low cost. If used as the main carbon source, methanol is added to a medium at a concentration of between 0.001 to 30%. As the nitrogen source, ammonium sulfate and so forth are added to the medium. In addition to these, trace-amount components such as potassium phosphate, sodium phosphate, magnesium sulfate, ferrous sulfate and manganese sulfate can be added in small amounts.

The culture is usually performed under aerobic conditions by shaking or aeration agitation while the pH is maintained between 5 and 9, and the temperature is maintained between 20 to 45° C., and it is typically complete within 24 to 120 hours.

L-lysine or L-arginine can usually be collected from the culture by a combination of an ion exchange resin method, precipitation method and other known methods.

EXAMPLES

Hereinafter, the present invention will be explained more specifically with reference to the preferred embodiments, given only by way of example.

Reagents produced by Wako Pure Chemical Industries or Nakarai Tesque were used unless otherwise specified. The compositions of media used in the examples are shown below. As for all the media, pH was adjusted with NaOH, KOH or HCl.

LB Medium:

| Bacto trypton (Difco) | 10 g/L |
| Yeast extract (Difco) | 5 g/L |
| NaCl | 10 g/L |
| pH 7.0 | |

Steam sterilization was performed at 120° C. for 20 minutes

LB Agar Medium:

LB Medium

| Bacto agar | 15 g/L |

Steam sterilization was performed at 120° C. for 20 minutes

SEII Medium:

| | |
|---|---|
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 μg/L |
| $MnSO_4 \cdot 5H_2O$ | 25 μg/L |
| $ZnSO_4 \cdot 7H_2O$ | 23 μg/L |
| $CaCl_2 \cdot 2H_2O$ | 72 mg/L |
| $FeCl_3 \cdot 6H_2O$ | 9.7 mg/L |
| $CaCO_3$ (Kanto Kagaku) | 30 g/L |
| Methanol | 2% (v/v) |
| pH 7.0 | |

The components other than methanol were subjected to steam sterilization at 121° C. for 15 minutes, and methanol was added after the medium was sufficiently cooled SEII Agar Medium:

| | |
|---|---|
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 μg/L |
| $MnSO_4 \cdot 5H_2O$ | 25 μg/L |
| $ZnSO_4 \cdot 7H_2O$ | 23 μg/L |
| $CaCl_2 \cdot 2H_2O$ | 72 mg/L |
| $FeCl_3 \cdot 6H_2O$ | 9.7 mg/L |
| Methanol | 0.5% (v/v) |
| pH 7.0 | |
| Bacto agar (Difco) | 15 g/L |

The components other than methanol were subjected to steam sterilization at 121° C. for 15 minutes, and methanol was added after the medium was sufficiently cooled Example 1

Construction of Mutant lysE Gene Library

First, the lysE gene, a homologous gene of the gene enhancing the secretion of L-lysine known for *Corynebacterium* bacteria, was cloned from a *Brevibacterium* bacterium, and expression of the gene was attempted in a *Methylophilus* bacterium.

(1) Construction of pRSlysE

In order to introduce lysE into a *Methylophilus* bacterium, a known plasmid pRS (see International Patent Publication in Japanese (Kohyo) No. 3-501682) was used to construct a plasmid pRSlysE for expression of lysE. pRS is a plasmid having the vector segment of the pVIC40 plasmid (International Patent Publication WO90/04636, International Patent Publication in Japanese No. 3-501682) and obtained from pVIC40 by deleting a DNA region encoding the threonine operon contained in the plasmid. The plasmid pVIC40 is derived from a broad host spectrum vector plasmid pAYC32 (Chistorerdov, A. Y., Tsygankov, Y. D., Plasmid, 1986, 16, 161-167), which is a derivative of RSF1010.

Specifically, pRS was constructed as follows. The pVIC40 plasmid was digested with EcoRI and added with a phenol/chloroform solution and mixed with it to terminate the reaction. After the reaction mixture was centrifuged, the upper layer was collected, and DNAs were collected by ethanol precipitation and separated on 0.8% agarose gel. A DNA fragment of about 8 kilobase pairs (hereinafter, "kbp") containing the vector side was collected by using DNA collecting kit EASY TRAP Ver. 2 (Takara Shuzo). The vector region fragment of the pVIC40 plasmid prepared as described above was self-ligated by using DNA Ligation Kit Ver. 2 (Takara Shuzo). This ligation reaction solution was used to transform *Escherichia coli* (*E. coli* JM109 competent cells, Takara Shuzo). The cells were applied on the LB agar medium containing 20 mg/L of streptomycin and incubated overnight at 37° C. The colonies that appeared on the agar medium were each inoculated to the LB liquid medium containing 20 mg/L of streptomycin and cultured at 37° C. for 8 hours with shaking. Plasmid DNA was extracted from each culture broth by the alkaline SDS method, and structure of each plasmid was confirmed by digestion with restriction enzymes to obtain pRS.

Then, a plasmid pRStac having the tac promoter was constructed from pRS according to the scheme shown in FIG. 1. The pRStac plasmid was constructed as follows. The pRS vector was digested with restriction enzymes EcoRI and PstI, and added to a phenol/chloroform solution and mixed to termininate the reaction. After the reaction mixture was centrifuged, the upper layer was collected, and DNAs were collected by ethanol precipitation and separated on 0.8% agarose gel. A DNA fragment of 8 kilobase pairs (henceforth abbreviated as "kbp") was collected by using DNA collection kit EASY TRAP Ver. 2 (Takara Shuzo). On the other hand, the tac promoter region was amplified by PCR using the pKK223-3 plasmid (expression vector, Pharmacia) as a template and the primers shown in SEQ ID NOS: 7 and 8 (a cycle consisting of denaturation at 94° C. for 20 seconds, annealing at 55° C. for 30 seconds and extension reaction at 72° C. for 60 seconds was repeated for 30 cycles). DNA polymerase PYROBEST (Takara Shuzo) was used for PCR. The DNA fragment containing the amplified tac promoter was purified by using PCR prep (Promega) and then digested at the restriction enzyme sites preliminarily designed in the primers, i.e., at EcoRI and EcoT22I sites. Then, the reaction mixture was added to a phenol/chloroform solution and mixed to terminate the reaction. After the reaction mixture was centrifuged, the upper layer was collected and DNAs were collected by ethanol precipitation and separated on 0.8% agarose gel. A DNA fragment of about 0.15 kbp was collected by using DNA collecting kit EASY TRAP Ver. 2 (Takara Shuzo).

The digestion products of the pRS vector and the tac promoter region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes to obtain pRStac. A plasmid in which the transcription directions of the streptomycin resistance gene on the pRS vector and the tac promoter were identical to each other was selected as pRStac.

pRStac obtained as described above was digested with Sse8387I (Takara Shuzo) and SapI (New England Biolabs), added to a phenol/chloroform solution and mixed to terminate the reaction. After the reaction mixture was centrifuged, the upper layer was collected and DNAs were collected by ethanol precipitation and separated on 0.8% agarose gel to obtain a DNA fragment of about 9.0 kbp.

The lysE gene fragment was also amplified by PCR using chromosome extracted from the *Brevibacterium lactofermentum* 2256 strain (ATCC13869) as a template and the primers shown in SEQ ID NOS: 9 and 10 (denaturation at 94° C. for 20 seconds, annealing at 55° C. for 30 seconds and extension reaction at 72° C. for 90 seconds). DNA polymerase PYROBEST (Takara Shuzo) was used for PCR. At this time, so that expression of the lysE gene is possible in a *Methylophilus* bacterium, the primers were designed so that nucleotides located 9-15 bp from the translation initiation codon of the lysE gene were replaced with a sequence that is known to function in a *Methylophilus* bacterium (Wybom, N. R., Mills, J., Williamis, S. G. and Jones, C. W., Eur. J. Biochem., 240, 314-322 (1996)). The obtained fragment was purified by using PCR prep (Promega) and then digested with Sse8387I and SapI. The reaction mixture was added to a phenol/chloroform solution and mixed to terminate the reaction. After the reaction mixture was centrifuged, the upper layer was collected and DNAs were collected by ethanol precipitation and further collected from 0.8% agarose gel.

The digestion products of the pRStac vector and the lysE gene region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and the structure of each plasmid was confirmed by digestion with restriction enzymes and determination of nucleotide sequence to obtain pRSlysE (FIG. 1). In pRSlysE, the lysE gene was positioned so that its transcription direction should be the same as that of the tac promoter.

(2) Introduction of pRSlysE into *Methylophilus* Bacterium p pRSlysE obtained as described above was introduced into *Methylophilus methylotrophus* AS1 strain (NCIMB10515) by electroporation (Canadian Journal of Microbiology, 43, 197 (1997)). In addition, pRS was also introduced into the AS1 strain as a control in the same manner as that for pRSlysE. As a result, several thousands of colonies were obtained per 1 µg of DNA with pRS used as a control, whereas only several colonies were obtained with pRSlysE.

When plasmids were extracted from transformant strains estimated to be introduced with pRSlysE and their nucleotide sequences were investigated, a spontaneous mutation was introduced in a region encoding lysE for all the investigated plasmids, and in some cases, a nonsense mutation was introduced as the mutation, by which a codon encoding an amino acid was replaced with a stop codon that terminated the translation. Furthermore, in the other plasmid, deletion of lysE gene was observed. It was considered that the function of lysE carried by such plasmids should be lost As described above, the introduction frequency of pRSlysE carrying the full length lysE gene into *Methylophilus methylotrophus* was extremely low, and only plasmids having a lysE mutant gene containing a mutation that eliminated the function could be introduced. Considering these facts in combination, it was estimated that the introduction of the lysE gene into *Methylophilus methylotrophus* was a lethal effect. This indicates that the lysE gene cannot universally function for the secretion of L-lysine in heterogenous bacteria.

The *Methylophilus methylotrophus* AS1strain harboring pRSlysE introduced with a mutation was applied to an SEII plate containing 50 mg/L of streptomycin and cultured overnight at 37° C. Then, the cells from about 10 cm² of the medium surface were scraped, inoculated into SEII production medium (20 ml) containing 50 mg/L of streptomycin, and cultured at 37° C. for 34 hours with shaking. After completion of the culture, the cells were removed by centrifugation and the L-lysine concentration in the culture supernatant was determined by using an amino acid analyzer (Nihon Bunko, high speed liquid chromatography). As a result, substantially no strain was obtained in which secretion of L-lysine was enhanced in spite of introduction of the mutant lysE gene.

As described above, the introduction of the already known lysE gene derived from *Corynebacterium* bacteria into methanol-assimilating bacteria results in a lethal effect. In the strains having a lysE gene introduced in only a small number, the introduced lysE gene suffered from mutation or deficiency, and lysE could not function. Since proteins responsible for secretion of amino acids function only when incorporated into a cell membrane, the protein and membrane conditions such as lipid composition must be mutually suitable. Therefore, it was considered difficult to express a membrane protein derived from an heterologous organism in such a way that its function was maintained. Accordingly, it was estimated that, if an artificial mutation introduction method was used by which more mutations can be positively introduced than natural mutations, a mutant lysE having L-lysine secretion ability could be successfully obtained from such mutants. Based on this concept, a mutant lysE library was constructed by using a mutation introduction method using hydroxylamine as described herein.

Furthermore, the inventors of the present invention considered that if a mutant lysE gene exhibiting L-lysine secretion activity in a methanol-assimilating bacterium was introduced into a methanol-assimilating bacterium, the degree of resistance to AEC (S-(2-aminoethyl)cysteine), an analogue compound of L-lysine, might be increased. Based on this concept, a screening system described herein was developed. First, the construction of the mutant lysE library will be described in detail.

(3) Mutation Treatment of pRSlysE Plasmid

The *E. coli* JM109 strain harboring the pRSlysE plasmid carrying wild-type lysE (available from Takara Shuzo) was inoculated to the LB liquid medium containing 20 mg/L of streptomycin and cultured at 37° C. for 8 hours with shaking. Each plasmid DNA was extracted from each culture broth by the alkaline SDS method.

Subsequently, a mutation was introduced into the prepared pRSlysE by an in vitro mutation method using hydroxylamnine. That is, a solution containing 250 mM potassium phosphate buffer adjusted to pH 6.0, 400 mM hydroxylamine solution adjusted to pH 6.0, each as a final concentration, and 2 µg of pRSlysE plasmid and made 200 µl water was prepared and incubated at 75° C. for 2 hours or 3 hours. Subsequently, the pRSlysE plasmid was collected from this solution by using DNA collection kit EASY TRAP Ver. 2 (Takara Shuzo). Plasmids reacted with hydroxylamine for 2 hours and plasmids reacted with hydroxylamine for 3 hours were mixed to obtain an aggregate of pRSlysE plasmids introduced with mutations at various rates.

The aggregate of mutant pRSlysE plasmids obtained as described above, which were estimated to be introduced with mutations at various positions, were amplified, and *Escherichia coli* (*E. coli* JM109 competent cells, Takara Shuzo) were transformed with this plasmid aggregate, applied on the LB agar medium containing 20 mg/L of streptomycin and incubated overnight at 37° C. to construct a library in *Escherichia coli*. All the colonies that appeared on the agar medium were scraped, inoculated to the LB liquid medium containing 20 mg/L of streptomycin and cultured at 37° C. for 8 hours with shaking. Plasmid DNA was extracted from each culture broth by the alkaline SDS method and used as a mutant pRSlysE plasmid library.

Introduction of Mutant pRSlysE Plasmid into *Methylophilus* Bacterium and L-amino Acid Production (1) Screening for Functional Type lysE from Library of lysE Introduced with Artificial Mutation The mutant pRSlysE plasmid library obtained as described above was introduced into the *Methylophilus methylotrophus* AS1 strain (NCIMB10515) by electroporation (Canadian Journal of Microbiology, 43, 197(1997)). As a control, wild-type pRSlysE was introduced into the As1 strain. As a result, with pRSlysE used as a control, the previous examination result was reproduced, and only several colonies were obtained per 1 μg of DNA. On the other hand, with the mutant pRSlysE plasmid library, several hundreds to several thousands of colonies could be obtained. The examinations so far have shown that, in almost all of the several colonies that appeared when wild-type pRSlysE was introduced, lysE lost the function due to the introduction of natural mutation. That is, the introduction frequency of pRSlysE carrying the full length lysE gene into *Methylophilus methylotrophus* was extremely low, and only plasmids having a mutant lysE gene containing a mutation that eliminated the function could be introduced. Considering these facts together, it was estimated that introduction of the lysE gene into *Methylophilus methylotrophus* would result in a lethal effect. On the other hand, since colonies far more than the above appeared when the mutant pRSlysE plasmid library was introduced, mutation introduction by hydroxylamine treatment was attained at a high efficiency.

As described above, the mutant lysE library could be obtained as a mutant pRSlysE plasmid library. Then, a screening system was developed for obtaining functional-type lysE, which expresses an activity for secreting L-lysine extracellularly.

The *Methylophilus methylotrophus* AS1 strain containing the mutant pRSlysE plasmid library obtained as described above was suitably diluted so that several hundreds of colonies per plate should appear, applied on the SEII agar medium containing 50 mg/L of streptomycin and 3 g/L of L-threonine and incubated at 37° C. for 48 hours. The colonies that appeared were replicated on the SEII agar medium containing 3 g/L of L-threonine and 0, 5, 7 or 10 g/L of AEC. When the colonies were replicated on a plate that did not contain AEC, the numbers of colonies that appeared on the original plate and the replicated plate after the replication were the same. However, when the colonies were replicated on the plate containing AEC, the number of colonies that appeared on the replicated plate markedly decreased as compared with that of the original plate. The colonies formed on the replicated plate containing AEC at each concentration were transferred to a new SEII agar medium containing AEC and cultured, and acquisition of AEC resistance was confirmed based on the observation that a single colony could be formed on the same medium. From such strains, 100 stains were randomly selected and subjected to further screening.

(2) L-amino Acid Production by Stain Introduced with Mutant pRSlysE Plasmid

Among the *Methylophilus methylotrophus* AS1 strains harboring a mutant pRSlysE estimated to be introduced with a mutation and to impart AEC resistance to a host, 100 strains were applied to an SEII plate containing 50 mg/L of streptomycin and cultured overnight at 37° C. Then, the cells on about 10 cm² of the medium surface were scraped, inoculated to an SEII production medium (20 ml) containing 50 mg/L of streptomycin and cultured at 37° C. for 48 hours with shaking. After completion of the culture, the cells were removed by centrifugation, and L-amino acids contained in the culture supernatant were isolated by thin layer chromatography and roughly quantified by a method utilizing detection with ninhydrin. As a result, it was found that L-lysine and L-arginine were extracellularly secreted at various concentrations. These 100 strains were roughly classified into 5 groups based on their patterns.

One typical strain was selected from each of these 5 groups, and the plasmids contained in these stains were designated as pRSlysE561, pRSlysE562, pRSlysE563, pRSlysE564 and pRSlysE565. These plasmids were purified, and the nucleotide sequences of their lysE regions were analyzed. As a result, it was found that pRSlysE562 and pRSlysE563, and pRSlysE561 and pRSlysE564 had completely identical sequences. Therefore, pRSlysE562, pRSlysE564 and pRSlysE565 were examined thereafter.

The nucleotide sequences of the regions encoding for the LysE protein in pRSlysE562, pRSlysE564 and pRSlysE565 were analyzed. As a result, it was found that lysE564 included substitution at the 166$^{th}$ position of A (adenine) for G (guanine) in the DNA sequence of wild-type lysE shown in SEQ ID NO: 1. As a result, Ser (serine) was substituted for Gly (glycine) at the 56$^{th}$ position in the amino acid sequence of wild-type lysE shown in SEQ ID NO: 2. It was also found that lysE562 included substitutions of A (adenine) for G (guanine) at the 166th position, and A (adenine) for G (guanine) at the 410$^{th}$ position in the DNA sequence of wild-type lysE shown in SEQ ID NO: 1. As a result, Ser (serine) was substituted for Gly (glycine) at the 56$^{th}$ (position and Gly (glycine) was substituted for Asp (aspartic acid) at the 137$^{th}$ position in the amino acid sequence of wild-type lysE shown in SEQ ID NO: 2. It was further found that lysE565 included substitutions of A (adenine) for G (guanine) at the 166$^{th}$ position and A (adenine) for G (guanine) at the 163$^{rd}$ position in the DNA sequence of wild-type lysE shown in SEQ ID NO: 1. As a result, Ser (serine) was substituted for Gly (glycine) at the 56$^{th}$ position and Thr (threonine) was substituted for Ala (alanine) 55$^{th}$ position in the amino acid sequence of wild-type lysE shown in SEQ ID NO: 2. When pRSlysE562, pRSlysE564 and pRSlysE565 were introduced into the AS1 strains again, these plasmids could be introduced at almost the same frequency as pRS. The plasmid-introduced strains were cultured by the same method as described above, and concentrations of L-lysine and L-arginine in the culture supernatants were quantified by using an amino acid analyzer (Nihon Bunko, high-performance liquid chromatography). The measurement results are shown in Table 1.

TABLE 1

| Bacterial strain | L-lysine production amount (g/L) | L-arginine production amount (g/L) |
|---|---|---|
| AS1/pRS | 0.01 | <0.010 |
| AS1/pRSlysE562 | 0.19 | 0.210 |

TABLE 1-continued

| Bacterial strain | L-lysine production amount (g/L) | L-arginine production amount (g/L) |
|---|---|---|
| AS1/pRSlysE564 | 0.20 | 0.240 |
| AS1/pRSlysE565 | 0.13 | 0.150 |

From the above results, it was found that pRSlysE562, pRSlysE564 and pRSlysE565 had activity for significantly increasing secretion of L-lysine and L-arginine. Furthermore, even when pRSlysE562, pRSlysE564 and pRSlysE565 were reintroduced into the AS1 strains, activity for increasing secretion L-lysine and L-arginine was maintained. Thus, it was demonstrated that the mutation of the AEC resistance-acquired strain was not introduced into the host, but into the plasmid.

The common mutation introduced into pRSlysE562, pRSlysE564 and pRSlysE565 was substitution of Ser (serine) for Gly (glycine) at the 56th position in the amino acid sequence of wild-type lysE shown in SEQ ID NO: 2. The E. coli JM109 strain transformed with pRSlysE564 having only this common mutation was designated AJ110086. This strain was deposited at International Patent Organism Depositary, National Institute of Advanced Industrial Science and Technology on Sep. 26, 2002 as an international deposit under the provisions of the Budapest Treaty and received an accession number of FERM BP-8196.

The lysE562 and lysE565 genes can be readily obtained from lysE564 by methods well known to those skilled in the art. Specifically, the lysE562 gene can be obtained by incorporating a fragment of the region encoding for lysE564 obtained from pRSlysE564 into, for example, pSELECTTM-1, a vector for site-directed mutation introduction produced by Promega, and introducing a site-directed mutation using Altered Sites™, a site directed mutation introduction kit produced by Promega, to substitute G (guanine) for A (adenine) at the 410$^{th}$ position in SEQ ID NO: 1. In the above procedure, for example, the synthetic oligonucleotide of SEQ ID NO: 5 can be used as a primer. The 20th nucleotide in SEQ ID NO: 5 is subject to nucleotide substitution in the wild-type lysE gene. Similarly, the lysE565 gene can be obtained by substituting A (adenine) for G (guanine) at the 166th position in SEQ ID NO: 1. For the mutation introduction, for example, the synthetic oligonucleotide of SEQ ID NO: 6 can be used. The 16th and 19th nucleotides in SEQ ID NO: 6 are subject to nucleotide substitution in the wild-type lysE gene.

Example 2

Introduction of L-lysine Biosynthesis Enzyme Gene and lysE562, lysE564 or lysE565 Gene into *Methylophilus methylotrophus*

Since it was found that the extracellular secretion of L-lysine was enhanced by the introduction of the lysE562, lysE564 or lysE565 genes, an L-lysine biosynthesis was enhanced in a strain introduced with the lysE562, lysE564 or lysE565 gene to attempt further improvement of the productivity.

(1) Construction of Plasmid pRSdapA having dapA* Gene

A plasmid having a gene encoding dihydrodipicolinate synthase that did not suffer feedback inhibition by L-lysine (dapA*) as an L-lysine biosynthesis system enzyme gene was prepared.

pRStac prepared in Example 1 was digested with Sse8387I and XbaI and added to a phenol/chloroform solution and mixed to terminate the reaction. After the reaction mixture was centrifuged, the upper layer was collected, and DNAs were collected by ethanol precipitation and separated on a 0.8% agarose gel to collect a DNA fragment of about 9 kbp.

The dapA* gene fragment was amplified by PCR using the known plasmid RSFD80 (see WO90/16042) containing that gene as a template and the primers shown in SEQ ID NOS: 11 and 12 (denaturation at 94° C. for 20 seconds, annealing at 55° C. for 30 seconds and extension reaction at 72° C. for 60 seconds). DNA polymerase PYROBEST (Takara Shuzo) was used for PCR. The resulting dapA* fragment was purified by using PCR prep (Promega) and then digested with restriction enzymes Sse8387I and XbaI. The reaction mixture was added to a phenol/chloroform solution and mixed to terminate the reaction. After the reaction mixture was centrifuged, the upper layer was collected, and DNAs were collected by ethanol precipitation and separated on a 0.8% agarose gel to collect a DNA fragment of about 0.1 kbp.

The digestion products of the pRStac vector and the dapA* gene region fragment prepared as described above were ligated by using DNA Ligation Kit Ver. 2 Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was exacted from each culture broth by the alkali-SDS method and the structure of each plasmid was confirmed by digestion with restriction enzymes and determination of the nucleotide sequence to obtain a pRSdapA plasmid. In pRSdapA plasmid, the dapA* gene was positioned so that its transcription direction should be the same as that of the tac promoter.

(2) Construction of Plasmid Having dapA* Gene and Any of lysE562, lysE564 or lysE565 Gene In order to evaluate the effect of combining any of lysE562, lysE564 or lysE565 with dapA*, plasmids pRSlysE562, pRSlysE564 and pRSlysE565 were constructed by insertion of the dapA* gene. pRSlysE562, lysE564 and lysE565 prepared in Example 1 were digested with a restriction enzyme SapI and blunt-ended by using DNA Blunting Kit (Takara Shuzo). Furthermore, a pRSdapA plasmid was digested with restriction enzymes EcoRI and SapI, and a fragment of about 1 kbp having the tac promoter and the dapA* region was separated on a 0.8% agarose gel and colleted by using DNA collecting kit EASY TRAP Ver. 2 (Takara Shuzo). This fragment was blunt-ended as described above and ligated to each of the digestion products of the aforementioned pRSlysE562, lysE564 and lysE565 by using DNA Ligation Kit Ver. 2 (Takara Shuzo).

*Escherichia coli* (*E. coli* JM109 competent cells, Takara Shuzo) was transformed with each of the aforementioned ligation reaction solutions, applied on the LB agar medium containing 20 mg/L of streptomycin and incubated overnight at 37° C. The colonies that appeared on the agar medium were inoculated into the LB liquid medium containing 20 mg/L of streptomycin and cultured at 37° C. for 8 hours with shaking. The plasmid DNA was extracted from each culture broth by the alkaline SDS method, and structure thereof was confirmed by digestion with restriction enzymes and determination of the nucleotide sequence to obtain pRSlysE562dapA, pRSlysE564dapA and pRSlysE565dapA plasmids. In these plasmids, the genes were positioned so that the transcription directions of lysE562, lysE564 and lysE565 should be opposite to that of dapA*.

When the pRSlysE562dapA, pRSlysE564dapA and pRSlysE565dapA plasmids obtained by the aforementioned method were each introduced into the *Methylophilus methylotrophus* AS1 strain (NCIMB10515) by electroporation, transformant strains were obtained with pRSlysE562dapA and pRSlysE564dapA, whereas no transformant strain was obtained with pRSlysE565dapA. This may be because stability of the plasmid decreased in the AS1 strain.

(3) Production of L-lysine by *Methylophilus* Bacteria Harboring lysE562 or lysE564 and dapA*

The AS1 strains introduced with pRSlysE562dapA or pRSlysE564dapA obtained as described above or pRSlysEdapA as a control were each applied to an SEII plate containing 20 mg/L of streptomycin and cultured overnight at 37° C., and the cells on 0.3 cm$^2$ of the medium surface were scraped, inoculated to the SEII production medium (20 ml) containing 20 mg/L of streptomycin and cultured at 37° C. for 34 hours with shaking. After completion of the culture, the cells were removed by centrifugation, and the concentration of L-lysine contained in the culture supernatant was quantified by using an amino acid analyzer (Nihon Bunko, high-performance liquid chromatography). The results are shown in Table 2. The strains introduced with pRSlysE562dapA or pRSlysE564dapA showed improved L-lysine accumulation. L-lysine accumulation in the media was markedly improved as compared with that introduced solely with pRSlysE562 or pRSlysE564. Thus, it can be seen that the rate limitation for the secretion was eliminated and the dapA* gene enhancing effect was synergistically exhibited.

TABLE 2

| Bacterial strain | L-Lysine production amount (g/L) |
|---|---|
| AS1/pRS | <0.10 |
| AS1/pRSlysE562dapA | 1.42 |
| AS1/pRSlysE564dapA | 1.40 |

Example 3

Introduction of lysE564 Gene into *Methylobacillus glycogenes* and L-amino Acid Production (1) Preparation of pRS-lysE564-Tc It was decided to confirm whether lysE562, lysE564 and lysE565, which contain mutant lysE, function in *Methylobacillus* bacteria. For this purpose, lysE564 was selected, and pRSlysE564, a plasmid for expression of lysE564, was modified. The pRSlysE564 plasmid carries a streptomycin resistant gene. However, since *Methylobacillus glycogenes* is originally resistant to streptomycin, the pRSlysE plasmid cannot be screened. Therefore, a modified plasmid was constructed by inserting a tetracycline resistance gene into the pRSlysE plasmid that could be used in *Methylobacillus glycogenes*.

First, pRS-lysE564-Tc carrying the tetracycline resistance gene was constructed from pRSlysE564. The pRS-lysE564 plasinid was digested with a restriction enzyme EcoRI and added to a phenol/chloroform solution and mixed to terminate the reaction. The reaction mixture was centrifuged, and the upper layer was collected. DNAs were collected by ethanol precipitation, and the digested ends thereof were blunt-ended by using DNA Blunting Kit (Takara Shuzo). DNA fragments were separated on a 0.8% agarose gel, and a DNA fragment having about 9 kilobase pairs (henceforth abbreviated as "kbp") was collected by using DNA collection kit EASY TRAP Ver. 2 (Takara Shuzo).

Furthermore, the tetracycline resistance gene region was amplified by PCR using the pRK310 plasmid (Pansegrau et al., J. Mol. Biol. 239, 623-663 (1994) as a template and the primers shown in SEQ ID NOS: 13 and 14 (a cycle consisting of denaturation at 94° C. for 20 seconds, annealing at 55° C. for 30 seconds and extension reaction at 72° C. for 60 seconds was repeated for 30 cycles). DNA polymerase PYROBEST (Takara Shuzo) was used for PCR. The amplified DNA fragment containing the tetracycline resistance gene region was purified by using PCR prep (Promega), and then DNAs were collected by ethanol precipitation, blunt-ended and phosphorylated by using Blunting Kination Ligation Kit TaKaRa BKL Kit (Takara Shuzo), added to a phenol/chloroform solution and mixed to terminate the reaction. After the reaction mixture was centrifuged, the upper layer was collected, and DNAs were collected by ethanol precipitation and separated on a 0.8% agarose gel. A DNA fragment of 1.5 kbp was collected by using DNA collecting kit EASY TRAP Ver. 2 (Takara Shuzo).

The tetracycline resistance gene can also be obtained by a PCR method similar to the above method by using another plasmid, for example, the pRK2 plasmid, as a template instead of pRK310.

The pRSlysE564 vector fragment prepared as described above and the DNA fragment containing the tetracycline resistance gene region were ligated by using DNA Ligation Kit Ver. 2 (Takara Shuzo). *Escherichia coli* (*E. coli* JM109 competent cells, Takara Shuzo) was transformed with this ligation reaction solution, applied on the LB agar medium containing 20 mg/L of streptomycin and 15 mg/L of tetracycline and cultured overnight at 37° C. The colonies that appeared on the agar medium were inoculated to the LB liquid medium containing 20 mg/L of streptomycin and 15 mg/L of tetracycline and cultured at 37° C. for 8 hours with shaking. Plasmid DNA was extracted from each culture broth by the alkaline SDS method, and the structure of each plasmid was confirmed by digestion with restriction enzymes to obtain pRS-lysE564-Tc.

(2) Introduction of pRS-lysE564-Tc into *Methylobacillus* Bacterium and L-amino Acid Production pRS-lysE564-Tc obtained as described above was introduced into the *Methylobacillus glycogenes* NCIMB11375 strain by electroporation (Canadian Journal of Microbiology, 43, 197 (1997)). As a control, pRK310 was similarly introduced into the *Methylobacillus glycogenes* NCIMB11375 strain. As a result, colonies containing pRS-lysE564-Tc were obtained at almost the same frequency as those obtained with pRK310, the control.

pRSlysET was constructed by inserting a tetracycline resistance gene region into the pRSlysE plasmid carrying wild-type lysE in the same manner as for pRS-lysE564-Tc, and it was attempted to introduce it into the *Methylobacillus glycogenes* strain in the same manner. However, no strain introduced with it was obtained. This is the same phenomenon observed in the *Methylophilus methylotrophus* AS1 strain, and it was estimated that wild-type lysE did not normally function also in *Methylobacillus* bacteria.

The *Methylobacillus glycogenes* NCIMB11375 strain harboring pRS-lysE564-Tc was applied to an SEII plate containing 10 mg/L of tetracycline and cultured overnight at 30° C. Then, the cells on about 10 cm$^2$ of the medium surface were scraped and inoculated to the SEII production medium (20 ml) containing 10 mg/L of tetracycline and cultured at 30° C. for 60 hours with shaking. After completion of the culture, the cells were removed by centrifugation, and the concentration of L-lysine contained in the culture supernatant was quantified using an amino acid analyzer (Nihon Bunko, high-performance liquid chromatography). The results are shown in Table 3.

TABLE 3

| Bacterial strain | L-lysine production amount (g/L) |
| --- | --- |
| NCIMB11375/pRK310 | 0.10 |
| NCIMB11375/pRS-lysE564-Tc | 1.40 |

(3) Construction of pRS-lysE564-dapA-Tc

It was found that L-lysine accumulated in a medium by introducing the lysE564 gene into the *Methylobacillus glycogenes* strain. It was considered that this was due to the enhancement of L-lysine secretion.

Accordingly the effect of enhancement on expression of a L-lysine biosynthesis gene and the lysE564 gene in combination in *Methylobacillus glycogenes* was examined in the same manner as in Example 2.

A plasmid was constructed by incorporating the tetracycline resistance gene into the pRSlysE564dapA plasmid prepared in Example 2, (2) by the same method as in Example 3, (1). The obtained plasmid was designated as pRS-lysE564-dapA-Tc.

(4) Introduction of pRS-lysE564-dapA-Tc Plasmid into *Methylobacillus glycogenes* and L-amino Acid Production pRS-lysE564-dapA-Tc obtained as described above was introduced into the *Methylobacillus glycogenes* NCIMB11375 strain by electroporation. The L-amino acid concentrations in the culture broth supernatants were examined for the obtained transformant strain (henceforth also refereed to as "NCIMB11375/pRS-lysE564-dapA-Tc"), the aforementioned *Methylobacillus glycogenes* strain introduced with pRS-lysE564-Tc (henceforth also refereed to as "NCIMB11375/pRS-lysE564-Tc") and the *Methylobacillus glycogenes* strain introduced with the pRK310 plasmid as a control (henceforth also referred to as "NCIMB11375/pRK310").

Each transformant strain was cultured on an SEII plate containing 10 mg/L of tetracycline for two days at 30° C. Then, the cells on 10 cm² of the medium surface were scraped and inoculated to the SEII production medium (20 ml) containing 10 mg/L of tetracycline and cultured at 30° C. for 60 hours with shaking. After completion of the culture, the cells were removed from a part of the culture broth by centrifugation, and the concentrations of L-amino acids contained in the culture supernatant were quantified by using an amino acid analyzer.

The results are shown in Table 4. A marked amount of L-lysine was accumulated in the medium containing the strain introduced with NCIMB11375/pRS-lysE564-dapA-Tc. The L-lysine accumulation in the medium containing the strain introduced with NCIMB11375/pRS-lysE564-dapA-Tc was improved as compared with the case where pRSlysE564T is solely introduced. It was considered that the rate limitation for the secretion was eliminated due to the introduction of the lysE564 gene, and the dapA* gene enhancing effect was synergistically exhibited.

TABLE 4

| Bacterial strain | L-lysine concentration in culture supernatant (g/L) |
| --- | --- |
| NCIMB11375/pRK310 | 0.20 |
| NCIMB11375/pRSlysE564T | 1.40 |
| NCIMB11375/pRS-lysE564-dapA-Tc | 1.62 |

While the invention has been described in detail with reference to preferred embodiments thereof, it will be apparent to one skilled in the art that various changes can be made, and equivalents employed, without departing from the scope of the invention Each of the aforementioned documents is incorporated by reference herein in its entirety, including the foreign priority document, JP2002-336315.

Explanation of Sequence Listing:
SEQ ID NO: 1: Wild-type lysE nucleotide sequence
SEQ ID NO: 2: Wild-type LysE amino acid sequence
SEQ ID NO: 3: Wild-type dapA nucleotide sequence
SEQ ID NO: 4: Wild-type DDPS amino acid sequence
SEQ ID NOS: 5 and 6: Primers for lysE562 site-specific mutation
SEQ ID NOS: 7 and 8: Primers for tac promoter amplification
SEQ ID NOS: 9 and 10: Primers for cloning of lysE
SEQ ID NOS: 11 and 12: Primers for cloning of dapA*
SEQ ID NOS: 13 and 14: Primers for amplification of tetracycline resistance gene region

What is claimed is:

1. An isolated DNA encoding a mutant LysE protein, wherein said mutant is selected from the group consisting of:
   A) a protein comprising the amino acid sequence of SEQ ID NO: 2 except that the glycine residue at position 56 is replaced with another amino acid residue, and
   B) a protein comprising the amino acid sequence of SEQ ID NO: 2 except that
      i) the glycine residue at position 56 of SEQ ID NO: 2 is replaced with another amino acid residue, and
      ii) not more than 10 amino acid residues at positions other than the 56th residue are substituted, deleted, or inserted, wherein said mutant imparts resistance to S-(2-aminoethyl) cysteine when introduced into a methylotroph.

2. The DNA of claim 1, wherein said DNA is selected from the group consisting of:
   A) a DNA which has the nucleotide sequence of SEQ ID NO: 1, except that a mutation which results in replacement of the 56th glycine residue of the encoded protein with another amino acid residue; and
   B) a DNA which is hybridizable with the nucleotide sequence of SEQ ID NO: 1 under stringent conditions comprising washing in 1×SSC and 0.1% SDS at 60° C.

3. The DNA of claim 1, wherein said glycine residue at position 56 is replaced with a serine residue.

4. The DNA of claim 1, wherein said methylotroph is a bacterium belonging to the genus *Methylophilis* or *Methylobacillus*.

5. A bacterium comprising the DNA of claim 1 in an expressible form, wherein said bacterium belongs to the genus *Methylophilus* or *Methylobacillus*, and wherein said bacterium has L-lysine or L-arginine producing ability.

6. A method for producing L-lysine or L-arginine comprising the steps of
   A) culturing the bacterium of claim 5 in a medium to produce L-lysine or L-arginine, and
   B) collecting L-lysine or L-arginine from the culture.

7. The method for producing L-lysine or L-arginine of claim 6, wherein the medium contains methanol as a major carbon source.

* * * * *